United States Patent [19]
Garland

[11] Patent Number: 5,846,076
[45] Date of Patent: Dec. 8, 1998

[54] SYSTEM FOR CASTING A DENTAL MODEL

[76] Inventor: James K. Garland, 3255 E. Seven Springs Dr., Sandy, Utah 84092

[21] Appl. No.: 990,511

[22] Filed: Dec. 15, 1997

[51] Int. Cl.[6] ........................................ A61C 11/00
[52] U.S. Cl. ................................... 433/60; 433/57
[58] Field of Search ................... 433/57, 60, 66

[56] References Cited

U.S. PATENT DOCUMENTS

| | | | |
|---|---|---|---|
| 565,326 | 8/1896 | Bragg | 433/60 |
| 2,911,722 | 11/1959 | Benfield et al. | 433/60 |
| 3,126,632 | 3/1964 | Weissman | 433/60 |
| 4,417,873 | 11/1983 | Kulas | 433/57 |
| 4,842,242 | 6/1989 | Huffman | 433/60 |
| 5,046,949 | 9/1991 | Richardson | 433/57 |
| 5,100,317 | 3/1992 | Darnand | 433/60 |
| 5,360,337 | 11/1994 | Westdyk | 433/57 |
| 5,403,185 | 4/1995 | Presswood | 433/57 |
| 5,658,143 | 8/1997 | Kuperman | 433/60 |

*Primary Examiner*—John J. Wilson
*Attorney, Agent, or Firm*—Terry M. Crellin

[57] ABSTRACT

A system for casting a dental model has first and second, hollow molds that are mounted on first and second mounting members. The mounting members have distal ends that extend into respective molds and proximal ends extending away from the molds. The molds are retained on and firmly held by the mounting members so that the molds can not rotate relative to the mounting members. Dental casting material can be poured into the molds and around the distal ends of the mounting members to form base stones in the molds. The mounting members are attached to connector members that extend from proximal ends of the mounting members. The other ends of the mounting members are pivotally connected to each other so that the molds can move between (i) a first position in which the central, horizontal planes of the molds are parallel and spaced apart from each other with the first mold positioned directly above the second mold, and (ii) a second position in which the first and second molds extend in substantially opposite directions away from each other.

6 Claims, 3 Drawing Sheets

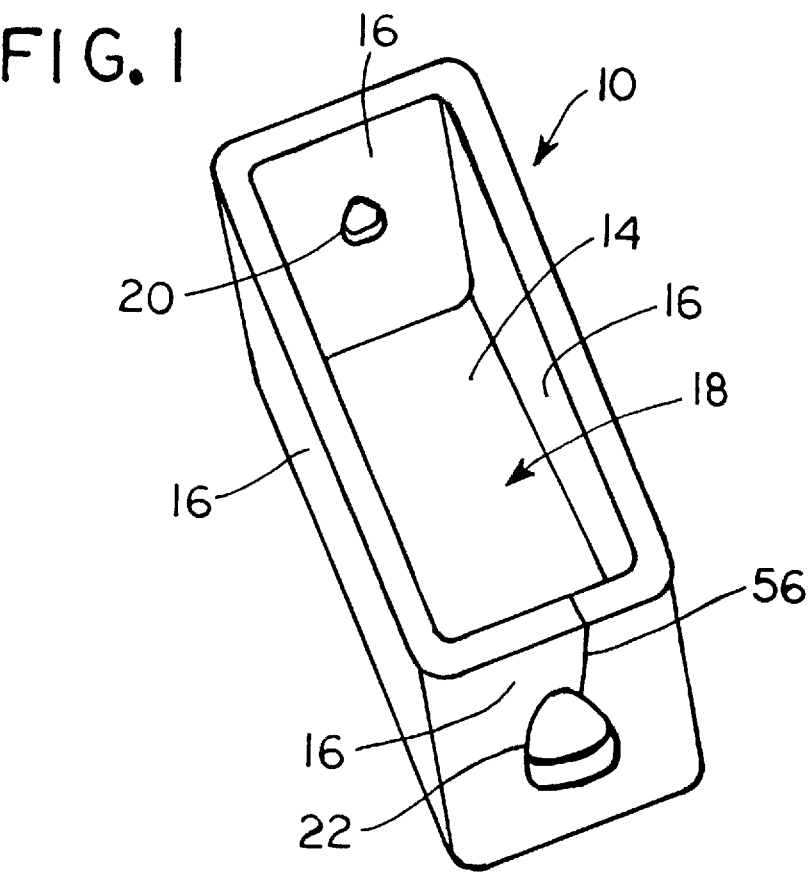
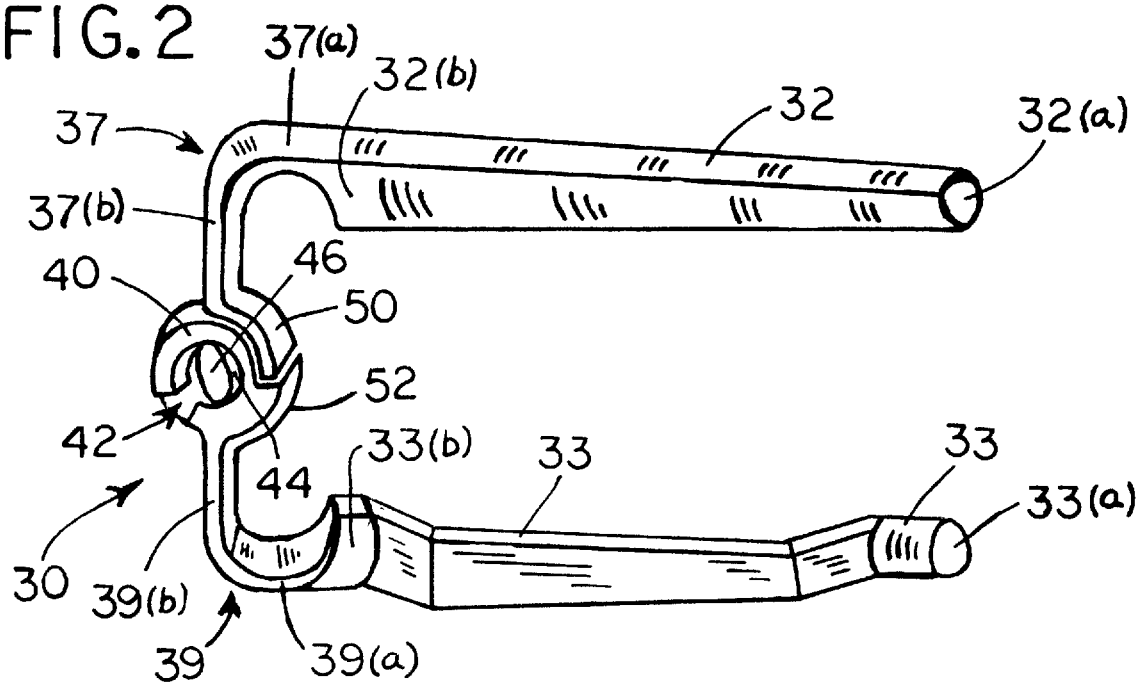

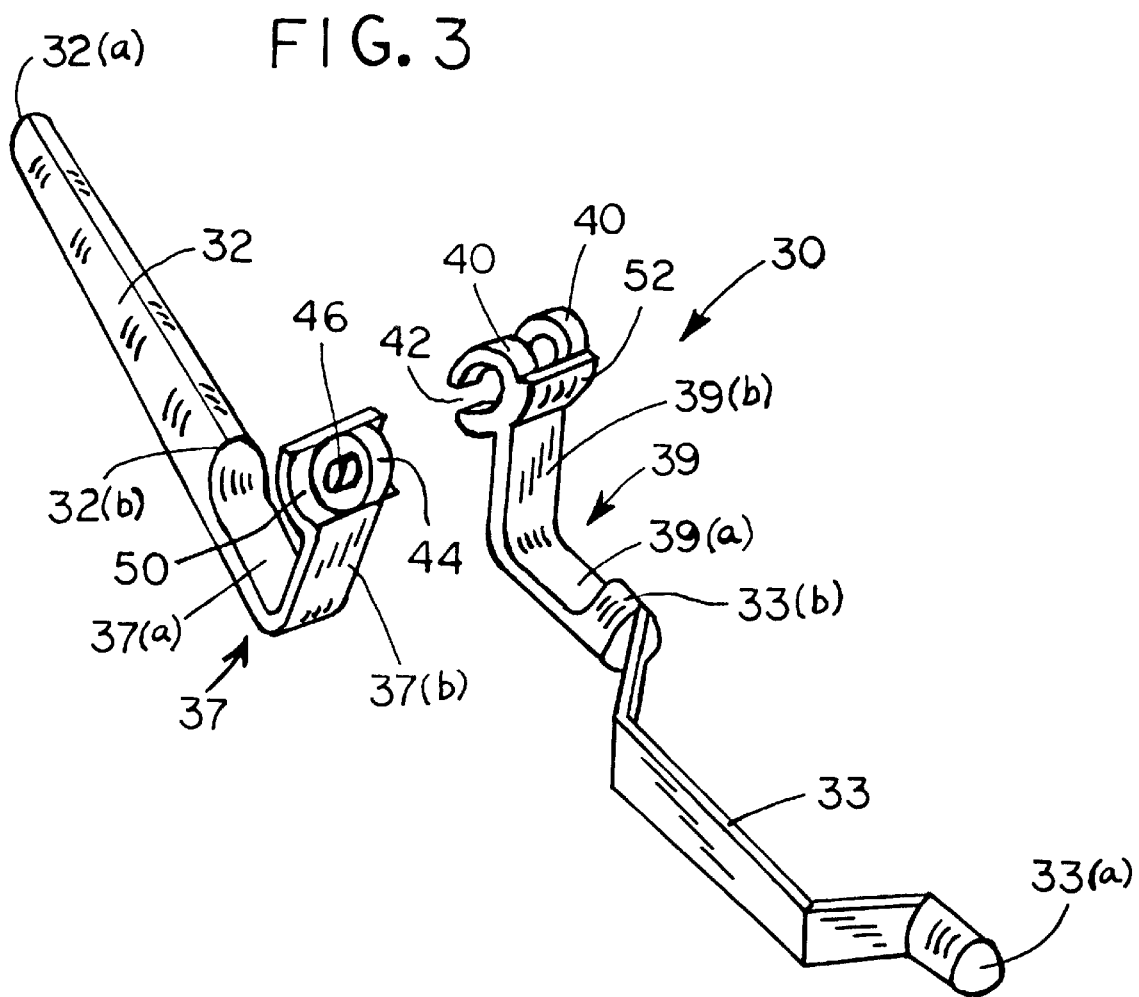

5,846,076

SYSTEM FOR CASTING A DENTAL MODEL

BACKGROUND OF THE INVENTION

1. Field of the Invention

The present invention relates generally to dental models and more particularly to a novel system for casting a dental model wherein base stones of the model are cast integrally to a unique articulation member. The base stones are cast in molds that are retained firmly on the articulation member as the base stones are being cast. The molds are restrained by the articulation member so that resulting cast base stones can be pivoted about the pivot axis of the articulation member from (1) a position in which the base stones are oriented one directly above the other in spaced apart relationship, with central, lateral, cross sections through the base stones lying in spaced apart, parallel planes to (2) a position in which the base stones extending away from each other with their central, lateral, cross sections lying in a common plane.

2. State of the Art

In order to fabricate a dental prosthetic, such as a crown, inlay, bridge etc., a negative impression of a patient's mouth is taken using an impression material, and a reproduction of the impression is made as a model in the dental laboratory. The reproduction is a solid, positive model of the gums and at least several adjacent teeth in the mouth, and it is necessary to support the reproduction on an articulation device to determine proper size, fit and movement of the restorative prosthetic relative to the other teeth of the patient.

The process of forming dental models is widely known and is described in U.S. Pat. No. 5,207,574 and will not be repeated here. Generally, the reproduction of the patient's teeth corresponding to the upper and lower teeth are formed on base stones in separate casting steps. The base stones are then affixed to an articulation device. There has been no suggestion in the prior art, at least to the present inventor's knowledge, of a system in which an articulation device can be separated into two pieces which can be rejoined to pivot about the ends that are joined together. There is further no suggestion of base molds being retained on the two pieces of the articulation device so that base stones of the model are cast directly about each of the two pieces of the articulation device. There is in particular no disclosure in the prior art of retaining the molds firmly on the two pieces of the articulation device as the base stones are being cast so that when the two pieces of the articulation device are joined together, the base stones will align one above the other, with the central, lateral cross sections of the two base stones lying in spaced apart, parallel planes.

BRIEF DESCRIPTION OF THE INVENTION

In accordance with the present invention, a novel system for casting a dental model is provided that combines a unique articulation component and two molds to cast base stones in place on mounting members of the articulation component. The system of the present invention includes a hollow, first mold made of an elastomeric material. The first mold has a bottom wall and side walls that extend from perimeter edges of the bottom wall to form an open-topped cavity in the first mold.

The articulation component comprises a first mounting member that has a distal end that extends into the cavity of the first mold. A proximal end of the first mounting member extends away from the first mold. It is important that the first mold is retained on and firmly held against movement by the first mounting member. The first mold must be retained and held firmly in a set position and orientation so that the first mold can not rotate or otherwise move relative to the first mounting member. This is essential because the first mounting member forms a part of the articulation combination, and to achieve proper articulation movement, the mold, and thus the base stone cast therein, must be carefully oriented and restrained in proper position during casting of the base stone. Dental casting material is poured into the cavity of the first mold and around the distal end of the first mounting member. The distal end of the first mounting member is embedded in and, thus, integrally attached to the resulting first base stone.

A first connector member is attached integrally to and extends from the proximal end of the first mounting member. The first mounting member and the first connector member form a first, distinct part of the articulation component of the present invention. These members support the first base stone when the base stone is cast about the mounting member. A second base stone must be cast, of course, and will now be explained.

A hollow, second mold is provided. The second mold is made of an elastomeric material and has a bottom wall and side walls that extend from perimeter edges of the bottom wall to form an open-topped cavity in the second mold. A second mounting member has a distal end that extends into the cavity of the second mold. A proximal end of the second mounting member extends away from the second mold. It is again important that the second mold is retained on and firmly held against movement by the second mounting member. Similar to the first mold, the second mold must be retained and held firmly in a set position and orientation so that the second mold can not rotate relative to the second mounting member. Dental casting material is poured into the cavity of the second mold and around the distal end of the second mounting member. The distal end of the second mounting member is embedded and, thus, integrally attached to the resulting second base stone.

A second connector member is attached integrally to and extends from the proximal end of the second mounting member. The second mounting member and the second connector member form the second distinct part of the articulation component of the present invention. These members support the second base stone when the base stone is cast about the second mounting member. The first and second connecting members are provided with means for pivotally connecting those members together to complete the articulation component.

The means for pivotally connecting the first connector member to the second connector member performs two essential functions. First, the first and second connector members must be connected together for pivotal movement of those members about the connecting means. Second, the first and second connector members must be capable of being disconnected from each other as well as connected to each other.

When the system of the present invention is used to cast the two base stones, and when the first and second connector members are connected with each other, the first and second connector members and the first and second molds can pivot about the means for pivotally connecting the first and second connector members. The base stones can then rotate between (i) a first position in which the central, horizontal planes of the first and second molds (and thus the base stones cast in the molds) are parallel and spaced apart from each other so that the first mold (and thus the first base stone cast in the mold) is positioned directly above the second mold (and thus the second base stone cast in that mold), with leading ends of the first and second molds (and thus the first and second base stones) lying on a line that is substantially perpendicular to the central, horizontal planes of the first and second molds (and thus the first and second base stones), and (ii) a second position in which the first and second molds (and thus the first and second base stones) extend in substantially opposite directions away from each other.

Additional objects and features of the invention will become apparent from the following detailed description, taken together with the accompanying drawings.

THE DRAWINGS

A preferred embodiment of the present invention representing the best mode presently contemplated of carrying out the invention is illustrated in the accompanying drawings in which:

FIG. 1 is a pictorial representation of a typical mold that can be used in the system of the present invention;

FIG. 2 is a pictorial view of the articulation device having mounting members each of which can have a mold attached thereto for casting a base stone directly on the mounting members;

FIG. 3 is a pictorial view of the articulation device of FIG. 2 showing the two components of the articulation device exploded to show details of the means of pivotally connecting the two components to each other;

DETAILED DESCRIPTION OF THE ILLUSTRATED EMBODIMENT

Figure 5:
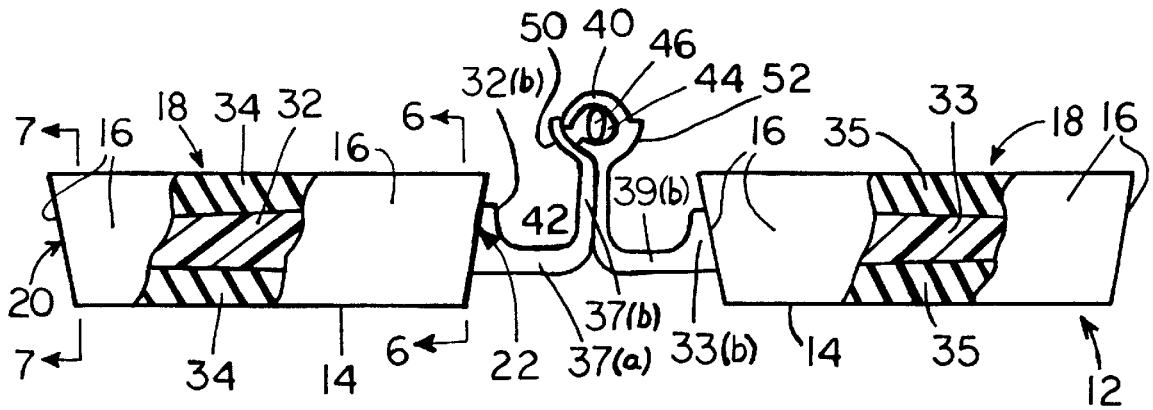
FIG. 5 is a side elevation of the articulation system of FIG. 3 but in which the molds are oriented so as to lie essentially flat and extending in opposite directions from each other, with the molds being shown partly in section to show base stones cast inside the molds.
Figure 4:
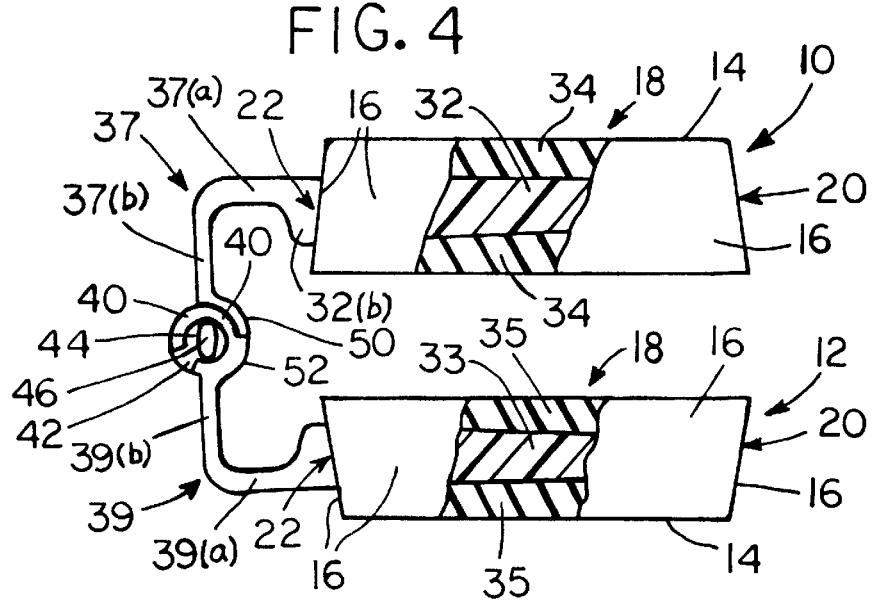
FIG. 4 is a side elevation of the articulation system of the present invention having molds attached thereto, with the molds oriented in spaced apart positions one mold being directly above the other mold.
Figure 6:
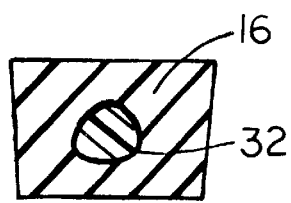
FIG. 6 is a cross section taken along line 6—6 of FIG. 4.
Figure 7:
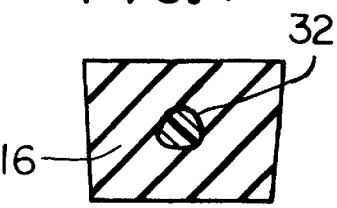
FIG. 7 is a cross section taken along line 7—7 of FIG. 4.

Referring now to FIGS. 1, 4 and 5 of the drawings, there are shown two hollow molds 10 and 12 that are used in the system for casting a dental model in accordance with the present invention. The two molds are essentially identical in construction. The first mold 10 is shown in isolation in FIG. 1 for purposes of description. The components of mold 10 are identical to those of mold 12, and like reference numbers are used for those components.

The first mold 10 is preferably made of an elastomeric material and has a bottom wall 14 and side walls 16 that extend from perimeter edges of the bottom wall 14. The bottom wall 14 and side walls 16 form a cavity 18 in the first mold 10 that has an open top. A first opening 20 extends inwardly into a side wall 16 of the first mold 10 from an inner face of the side wall 16. The first opening 20 has a perimeter that has a non-circular shape, with the first opening 20 further having a set orientation. As illustrated, the first opening is substantially triangular in shape, but the corners and the sides are curved rather than sharp and straight.

A second opening 22 extend through an opposite side wall 16 of the first mold 10. The second opening 22 has a perimeter that has a shape that corresponds to the non-circular shape of the first opening 20. The second opening 22 is oriented to have an orientation that is substantially identical with the orientation of the first opening 20. The orientation of the openings 20 and 22 is such that the openings are in alignment with one opening being linear projection of the other.

Referring now to FIGS. 2–8 of the drawings, a preferred embodiment of the articulation device 30 of the present invention comprises an elongate, first pin 32. The pin 32 is adapted to extend from the second opening 22 through the cavity 18 of the first mold 10 to the first opening 20. The leading end 32(a) of the first pin 32 has a shape and size corresponding to the shape and size of the first opening 20 so that the leading end 32(a) of the first pin 32 fits snugly within the first opening 20. The distal end 32(b) of the first pin 32 has a shape and size corresponding to the shape and size of the second opening 22 so that the distal end 32(b) of the first pin 32 fits snugly within the second opening 22 when the leading end 32(a) of the first pin 32 is received in the first opening 20.

When the leading end 32(a) of the first pin 32 engages the first opening 20 and the distal end 32(b) of the first pin 32 engages the second opening 22 in the first mold 10, the first pin 32 is held firmly in place extending longitudinally through the cavity 18 of the first mold 10 so that the first mold 10 can not rotate or otherwise move relative to the first pin 32 when dental casting material is poured into the cavity 18 and around the first pin 32 to form a first base stone 34 in the first mold 10. The first pin 32 is fully embedded in the first base stone 34, and the leading and distal ends 32(a) and 32(b) of the first pin 32 project from opposite ends of the first base stone 34.

A hollow, second mold 12 is provided (see FIGS. 4 and 5). The second mold 12 is made of an elastomeric material. Like the first mold 10, the second mold 14 has a bottom wall 14 and side walls 16 that extend from perimeter edges of the bottom wall 14. The bottom wall 14 and side walls 16 of the second mold 12 form a cavity 18 in the second mold 18 that has an open top.

A first opening 20 extends inwardly into a side wall 16 of the second mold 12 from an inner face of the side wall 16 of the second mold 12. The first opening 20 in the side wall 16 of the second mold 12 has a perimeter that has a non-circular shape, with the first opening 20 in the side wall 16 of the second mold 12 further having a set orientation.

A second opening 22 extend through an opposite side wall 16 of the second mold 12. The second opening 22 in the side wall 16 of the second mold 12 has a perimeter that has a shape that corresponds to the non-circular shape of the first opening 20 in the side wall 16 of the second mold 12. The second opening 22 in the side wall 16 of the second mold 12 is oriented to have the same orientation to that of the first opening 20 in the side wall 16 of the second mold 12.

An elongate, second pin 33 of the articulation device 30 extends from the second opening 22 in the side wall 16 of the second mold 12 through the cavity 18 of the second mold 12 to the first opening 20 in the side wall 16 of the second mold 12. The leading end 33(a) of the second pin 33 has a shape and size corresponding to the shape and size of the first opening 20 in the side wall 16 of the second mold 12 so that the leading end 33(a) of the second pin 33 fits snugly within the first opening 20 in the side wall 16 of the second mold 12.

The distal end 33(b) of the second pin 33 has a shape and size corresponding to the shape and size of the second opening 22 in the side wall 16 of the second mold 12 so that the distal end 33(b) of the second pin 33 fits snugly within the second opening 22 in the side wall 16 of the second mold 12 when the leading end 33(a) of the second pin 33 is received in the first opening 20 in the side wall 16 of the second mold 12. When the leading end 33(a) of the second pin 33 engages the first opening 20 in the side wall 16 of the second mold 12 and the distal end 33(b) of the second pin 33 engages the second opening 22 in the side wall 16 of the second mold 12, the second pin 33 is held firmly in place extending longitudinally through the cavity 18 of the second mold 12 so that the second mold 12 can not rotate or otherwise move relative to the second pin 33 when dental casting material is poured into the cavity 18 of the second mold 12 and around the second pin 33 to form a second base stone 35 in the second mold 12. The second pin 33 is fully embedded in the second base stone 35 so that the leading and distal ends 33(a) and 33(b) of the second pin 33 projects from opposite ends of the second base stone 35.

Means are provided for pivotally connecting one end of a first connector member 37 to a corresponding end of the second connector member 39 so that the first and second connector members 37 and 39 can be connected and disconnected from each other as well as pivot about their connected ends. The pivotal connecting means must allow the first and second connector members 37 and 39 to move so that longitudinal axes through the leading and distal ends of the first and second pins 32 and 33 are oriented to lie in a common plane. Further, the first and second connector members 37 and 39 must pivot about the means for pivotally connecting the first and second connector members 37 and 39 so that the longitudinal axes of the first and second pins 32 and 33 move in the common plane between (i) a first position in which the longitudinal axes of the first and second pins 32 and 33 are parallel and spaced apart from each other so that the first mold 10 is positioned directly above the second mold 12 (see FIG. 4), with leading ends of the first and second molds 10 and 12 lying on a line that is substantially perpendicular to the longitudinal axes of the first and second pins 32 and 33, and (ii) a second position in which the first and second pins 32 and 33 extend in substantially opposite directions away from each other so that the first and second molds 10 and 12 extend in substantially opposite directions away form each other (see FIG. 5).

As illustrated in drawings, the first connector member 37 preferably comprises a first L-shaped member having a relatively short section 37(a) and a relatively longer section 37(b). The shorter section 37(a) extends away from the distal end of the first pin 32 so as to be substantially parallel or coincident with the longitudinal axis of the first pin 32. The longer section 37(b) is oriented substantially perpendicular to the short section 37(a) of the first L-shaped member so that the free end of the longer section 37(a) extends away from the longitudinal axis of pin 32.

A second connector member 39 comprises a second L-shaped member having a relatively short section 39(a) and a relatively longer section 39(b). The shorter section 39(a) extends away from the distal end of the second pin 33 so as to be substantially parallel to or coincident with the longitudinal axis of the second pin 33. The longer section 39(a) is oriented substantially perpendicular to the short section 39(a) of the second L-shaped member so that the free end of the longer section 39(b) extends away from the longitudinal axis of pin 33.

The means for pivotally connecting the first connector member 37 to the second connector member 39 preferably comprises a pair of spaced apart, circular rings 40 extending from a free end of the longer section 39(b) of the second L-shaped member. The rings 40 are substantially parallel with each other. Each of the rings 40 have an opening 42 in the wall of each ring. The openings 42 extend from the perimeter of each of the rings 42 to a circular center space encircled by each of the rings 42. The openings 42 in the rings 40 are aligned in mating positions on the respective rings 40. The openings 42 lie spaced apart from each other on a straight line that is parallel with an axis through the centers of the circular center spaces encircled by each of the rings 40.

A circular disk 44 extends from a free end of the longer section 37(b) of the first L-shaped member. The circular disk 44 is adapted to fit snugly between the pair of rings 40. The circular disk 44 further has a pair of studs 46 extending from opposite flat sides thereof. The studs 46 are of a size that will slide through the openings 42 in the pair of rings 40 and fit snugly within the circular center spaces encircled by each of the rings 40 so that the circular disk 44 can rotate about an axis through the studs 46.

A mechanical stop mechanism is advantageously provided that restrains the pivotal movement of the connector members 37 and 39 when the pins 32 and 33 are aligned in their parallel position, one spaced directly above the other. As illustrated, raised arcuate sections 50 and 52 extend from the free ends of the connector members 37 and 39. The sections 50 and 52 encircle portions of the rings 40 and the disk 44, respectively. The sections 50 and 52 extend about ¼ of the circumference of each of the rings 40 and the disk 44. The distal ends of the sections 50 and 52 abut each other and form a stop when the rings 40 and disk 44 are pivoted to a position in which the pins 32 and 33 are aligned in their parallel orientation, one spaced directly above the other.

The system of the present invention is used to make dental models by placing the molds 10 and 12 on the pins 32 and 33. The leading ends of each of the pins 32 and 33 are pushed through each of the respective larger second openings 22 in the molds 10 and 12, and the pins 32 and 33 are pushed through the cavities 18 of the molds until the lead ends of the pins 32 and 33 engage the smaller first openings 20. Preferably, the smaller first openings 20 do not go completely through the side wall 16 of the molds 10 and 12. They have closed inner ends that act as a stop for the lead ends of the pins 32 and 33. When the lead ends of the pins 32 and 33 abut the closed ends of the first openings 20, the pins 32 and 33 fully engage and mate with the openings 20 and 22 so that the molds 10 and 12 are firmly retained on the respective pins 32 and 33.

Casting material is poured into each of the molds 10 and 12 to completely fill the cavities 18 of the molds and fully encapsulate the pins 32 and 33. The articulation system is then closed to the position in which the upper mold 10 is directly above the lower mold 12 as shown in FIG. 4. Casting material is then filled into an impression that has been prepared by a dentist. The impression (not shown in the drawings) is placed between the upper mold 10 and the lower mold 12 to allow the impression of the upper teeth to bond to the base stone 34 in the upper mold 10 and the impression of the lower teeth to bond to the base stone 35 in the lower mold 12. An elongate metal plate (not shown in the drawings) can be provided if desired to firmly hold the upper mold 10 and lower mold 12 in parallel, spaced orientation as the casting material of the base stones and impressions is setting. The plate is bent into a square cornered, U-shape, and the molds 10 and 12 are inserted into the open end of the U-shape so that the bottoms of the respective molds 10 and 12 are held in parallel with each other by the parallel legs of the U-shaped member.

After the casting material has been set, the molds 10 and 12 can be removed from the resulting dental model. To facilitate the removal of the molds 10 and 12 from their respective base stones, slits 56 are formed in the side wall 16. The slits 56 extend from the upper edge of the side wall 16 to the second openings 22. The slits 56 allow the side wall 16 of the molds to be pulled over the pins 32 and 33 when removing the molds 10 and 12 from the dental model.

Although a preferred embodiments of the system of the present invention has been illustrated and described, it is to be understood that the present disclosure is made by way of example and that various other embodiments are possible without departing from the subject matter coming within the scope of the following claims, which subject matter is regarded as the invention.

I claim:

1. A system for casting a dental model, said system comprising a hollow, first mold made of an elastomeric material, said first mold having a bottom wall and side walls that extend from perimeter edges of said bottom wall of said first mold to form a cavity in said first mold that has an open top;

a first opening extending inwardly into a side wall of said first mold from an inner face of said side wall, said first opening having a perimeter that has a non-circular shape, with said first opening further having a set orientation;

a second opening extending through an opposite side wall of said first mold, said second opening having a perimeter that has a shape that corresponds to the non-circular shape of said first opening, with said second opening being oriented to have an orientation that is substantially identical with the orientation of said first opening;

an elongate, first pin extending from said second opening through said cavity of said first mold to said first opening;

a leading end of said first pin has a shape and size corresponding to the shape and size of said first opening so that said leading end of said first pin fits snugly within said first opening;

a distal end of said first pin has a shape and size corresponding to the shape and size of said second opening so that said distal end of said first pin fits snugly within said second opening when said leading end of said first pin is received in said first opening, wherein when said leading end of said first pin engages said first opening and said distal end of said first pin engages said second opening, said first pin is held firmly in place extending longitudinally through said cavity of said first mold so that said first mold can not rotate relative to said first pin, whereby dental casting material can be poured into the cavity of said first mold and around said first pin to form a first base stone in said first mold, with said first pin being embedded in said first base stone so that the leading and distal ends of said first pin projects from opposite ends of said first base stone;

a first connector member attached integrally to and extending from said distal end of said first pin;

a hollow, second mold made of an elastomeric material, said second mold having a bottom wall and side walls that extend from perimeter edges of said bottom wall of said second mold to form a cavity in said second mold that has an open top;

a first opening extending inwardly into a side wall of said second mold from an inner face of said side wall of said second mold, said first opening in said side wall of said second mold having a perimeter that has a non-circular shape, with said first opening in said side wall of said second mold further having a set orientation;

a second opening extending through an opposite side wall of said second mold, said second opening in said side wall of said second mold having a perimeter that has a shape that corresponds to the non-circular shape of said first opening in said side wall of said second mold, with said second opening in said side wall of said second mold being oriented to have an orientation that is substantially identical with the orientation of said first opening in said side wall of said second mold;

an elongate, second pin extending from said second opening in said side wall of said second mold through said cavity of said second mold to said first opening in said side wall of said second mold;

a leading end of said second pin has a shape and size corresponding to the shape and size of said first opening in said side wall of said second mold so that said leading end of said second pin fits snugly within said first opening in said side wall of said second mold;

a distal end of said second pin has a shape and size corresponding to the shape and size of said second opening in said side wall of said second mold so that said distal end of said second pin fits snugly within said second opening in said side wall of said second mold when said leading end of said second pin is received in said first opening in said side wall of said second mold, wherein when said leading end of said second pin engages said first opening in said side wall of said second mold and said distal end of said second pin engages said second opening in said side wall of said second mold, said second pin is held firmly in place extending longitudinally through said cavity of said second mold so that said second mold can not rotate relative to said second pin, whereby dental casting material can be poured into the cavity of said second mold and around said second pin to form a second base stone in said second mold, with said second pin being embedded in said second base stone so that the leading and distal ends of said second pin projects from opposite ends of said second base stone;

a second connector member attached integrally to and extending from said distal end of said second pin; and means for pivotally connecting said first connector member to said second connector member so that (1) the first and second connector members can be connected and disconnected from each other, (2) when the first and second connector members are connected with each other, longitudinal axes through the leading and distal ends of said first and second pins are oriented so as to lie in a common plane, and (3) when the first and second connector members are connected with each other, said first and second connector members can pivot about said means for pivotally connecting said first and second connector members so that said longitudinal axes of said first and second pins move in said common plane between (i) a first position in which said longitudinal axes of said first and second pins are parallel and spaced apart from each other so that said first mold is positioned directly above said second mold, with leading ends of said first and second molds lying on a line that is substantially perpendicular to the longitudinal axes of said first and second pins, and (ii) a second position in which said first and second pins extend in substantially opposite directions away from each other so that said first and second molds extend in substantially opposite directions away form each other.

2. A system for casting a dental model in accordance with claim 1 wherein said second opening in said first mold is larger in cross-sectional size than the first opening in said first mold, and said second opening in said second mold is larger in cross-sectional size than the first opening in said second mold.

3. A system for casting a dental model in accordance with claim 1 wherein said first connector member extends away from said longitudinal axis of said first pin.

4. A system for casting a dental model in accordance with claim 3 wherein said second connector member extends away from said longitudinal axis of said second pin.

5. A system for casting a dental model in accordance with claim 4 wherein (1) said first connector member comprises
   a first L-shaped member having a relatively short section extending away from said distal end of said first pin and being substantially parallel to or coincident with said longitudinal axis of said first pin; and
   a longer section oriented substantially perpendicular to said short section of said first L-shaped member;

(2) said second connector member comprises
   a second L-shaped member having a relatively short section extending away from said distal end of said second pin and being substantially parallel to or coincident with said longitudinal axis of said second pin;
   a longer section oriented substantially perpendicular to said short section of said second L-shaped member; and (3) said means for pivotally connecting said first connector member to said second connector member comprises
   a pair of spaced apart, circular rings extending from a free end of said longer section of said first L-shaped member, said rings being substantially parallel with each other, said rings having an opening in each ring that extend from the perimeter of each ring to a circular center space encircled by each ring, with said openings in said rings being aligned with each other along a straight line that is parallel with an axis through the centers of said circular center spaces encircled by each of said rings; and
   a circular disk extending from a free end of said longer section of said second L-shaped member, said circular disk fitting snugly between said pair of rings, said circular disk further having a pair of studs extending from opposite flat sides thereof, with said studs being of a size that will slide through said openings in said pair of rings and fit snugly within said circular center spaces encircled by each of said rings so that said circular disk can rotate about an axis through said studs.

6. A system for casting a dental model, said system comprising
   a hollow, first mold made of an elastomeric material, said first mold having a bottom wall and side walls that extend from perimeter edges of said bottom wall of said first mold to form a cavity in said first mold that has an open top;
   a first mounting member having a distal end that extends into said first mold and a proximal end extending away from said first mold, with said first mold being retained on and firmly held by said first mounting member in a set position and orientation so that said first mold can not rotate relative to said first mounting member, whereby dental casting material can be poured into the cavity of said first mold and around the distal end of said first mounting member to form a first base stone in said first mold, with said distal end of said first mounting member being embedded in said first base stone;
   a first connector member attached integrally to and extending from said proximal end of said first mounting member;
   a hollow, second mold made of an elastomeric material, said second mold having a bottom wall and side walls that extend from perimeter edges of said bottom wall of said second mold to form a cavity in said second mold that has an open top;
   a second mounting member having a distal end that extends into said second mold and a proximal end extending away from said second mold, with said second mold being retained on and firmly held by said second mounting member in a set position and orientation so that said second mold can not rotate relative to said second mounting member, whereby dental casting material can be poured into the cavity of said second mold and around the distal end of said second mounting member to form a second base stone in said second mold, with said distal end of said second mounting member being embedded in said second base stone;
   a second connector member attached integrally to and extending from said proximal end of said second mounting member; and
   means for pivotally connecting said first connector member to said second connector member so that (1) the first and second connector members can be connected and disconnected from each other, and (2) when the first and second connector members are connected with each other, said first and second connector members and said first and second molds can pivot about said means for pivotally connecting said first and second connector members so that said first and second molds move between (i) a first position in which said central, horizontal planes of said first and second molds are parallel and spaced apart from each other so that said first mold is positioned directly above said second mold, with leading ends of said first and second molds lying on a line that is substantially perpendicular to the central, horizontal planes of said first and second molds, and (ii) a second position in which said first and second molds extend in substantially opposite directions away from each other.

* * * * *